United States Patent [19]
Everett

[11] Patent Number: 4,552,844
[45] Date of Patent: Nov. 12, 1985

[54] PLANT GROWTH MEDIUM

[75] Inventor: Nicholas P. Everett, El Sobrante, Calif.

[73] Assignee: Stauffer Chemical Company, Westport, Conn.

[21] Appl. No.: 504,355

[22] Filed: Jun. 15, 1983

[51] Int. Cl.$^4$ .......................... C12N 5/00; C12N 5/02; C12P 21/00; G01N 33/54
[52] U.S. Cl. .................................... 435/240; 435/241; 435/68; 435/948; 436/63
[58] Field of Search ................. 435/240, 241, 68, 948; 47/58; 436/63

[56] References Cited

U.S. PATENT DOCUMENTS 3,628,287  12/1971  Staba et al. ............................... 47/58
4,306,022  12/1981  Kinsella et al. ...................... 435/134

OTHER PUBLICATIONS

Russell, W. A., *Can. J. Agri. Sci.*, 1955, "A Study of the Inter-Relationships of Seed Yield, Oil Content, and Other Agronomic Characters with Sunflower Inbred Lines and Their Top Crosses".
Kesteloot, J. A., *Proc. 10th Int. Sunflower Conference*, Australia, 1982, "Morphological Differences Between High and Low Yielding Hybrids of Sunflower".
Skoric, *Proc. 10th Int. Sunflower Conf.*, Australia, 1982, "Correlations for Important Agronomic Characters Between . . . ".
Miller et al., *Proc. 10th Int. Sunflower Conf.* Australia, 1982, "Relationships Among Traits of Inbreds and Hybrids of Sunflower".
Gamborg Oluf et al., *Tissue Culture and Plant Science*, 1974, pp. 268–269, "Protoplasts and Tissue Culture Methods in Crop Plant Improvement".
Kruse, Paul et al., *Tissue Culture Methods and Applications*, 1973 Academic Press, N.Y., pp. 160, 216, 503.
Bokhorova, N. et al., *Chemical Abst.*, v. 94, No. 153572d, 1981, "In vitro Isolation of Anthers from Interspecies Hybrids in the Helianthus genus".

*Primary Examiner*—Thomas G. Wiseman
*Assistant Examiner*—Robin Lyn Teskin
*Attorney, Agent, or Firm*—Michael J. Bradley

[57] ABSTRACT

Artificial plant growth media suitable for suspension cell culture of sunflower plant cells are provided. Methods of using the media for growth of suspension cell culture of sunflower plant cells are provided. Methods for screening the oil content of sunflower seeds produced by sunflower plants utilizing the suspension cell growth characteristics of sunflower plant cells are provided.

6 Claims, 1 Drawing Figure

4,552,844

PLANT GROWTH MEDIUM

FIELD OF THE INVENTION

The invention relates to artificial plant growth media and methods of using the media for suspension cell culture and oil content screening.

BACKGROUND OF THE INVENTION

The improvement of field crops is a time-consuming, labor-intensive task that often requires extensive use of valuable cropland. Typically, a desirable characteristic is observed in a particular crop plant and is either cross-bred with another strain of the crop, selfed, or back-crossed with the parental line and then back-crossed with the parental line for numerous generations.

If the characteristics for which a breeding program is initiated is only manifest in the seed or fruit of the mature plant, the time and labor expended in evaluating the candidate in a particular breeding program are maximal. Oil content of sunflower fruits is a characteristic which has heretofore only been determinable by direct evaluation of the oil content of mature seed. Thus, evaluating the oil content of seed candidates in a sunflower seed oil breeding program using traditional methods utilized the resources of time, labor and land maximally.

A significant saving in these resources could be effected if it were possible to determine the seed oil content of sunflower seed candidates at a time prior to maturation of the sunflower plant. Preferably such determination would be carried out very early in the sunflower plant life cycle, would require little or no land and would require a minimum of time.

SUMMARY OF THE INVENTION

The inventor has discovered a basic plant growth medium which makes it possible to culture *Helianthus annuus* (*H. annuus*) in a suspension cell culture. The fruits or seeds of *H. annuus* are the source of sunflower seed oil. Thus, the utility of the medium lies in its ability to allow suspension cell culture of *H. annuus*, an important oil-producing crop plant, and the manipulation of such cells for the purpose of improving the strain.

Furthermore, the inventor has also discovered that when the cells of sunflower tissue are cultured in the suspension medium, the growth characteristics of the cells in culture can be correlated with a high degree of confidence with the oil content of the seeds of the whole plant. In particular, it has been discovered that suspension cell cultures may be initiated from hypocotyl segments of sunflower plant seedlings. Moreover, suspension cell cultures may be initiated from callus derived from practically any sunflower tissue, including those derived from seedlings and fully grown plants. Thus, the medium can be employed in a method of screening prospective sunflower seed lines for oil content without the labor, land use, or time requirements of field trials of the sunflower seed plant. Additionally, the cell suspension culture method can be used to narrow the number of prospective sunflower seed lines to be field-tested to a far smaller group of seed lines which has a high probability of having high oil content.

It will be readily apparent to those skilled in the art of plant tissue culture that the above briefly described method of suspension culture of sunflower plant cells has a broad potential for allowing the alteration, growth and selection of single sunflower plant cells that have been genetically altered by a variety of means, including physical and chemical mutagenesis or transformation using deoxyribonucleic acid (DNA) from organisms other than the sunflower plant.

Figure 1:
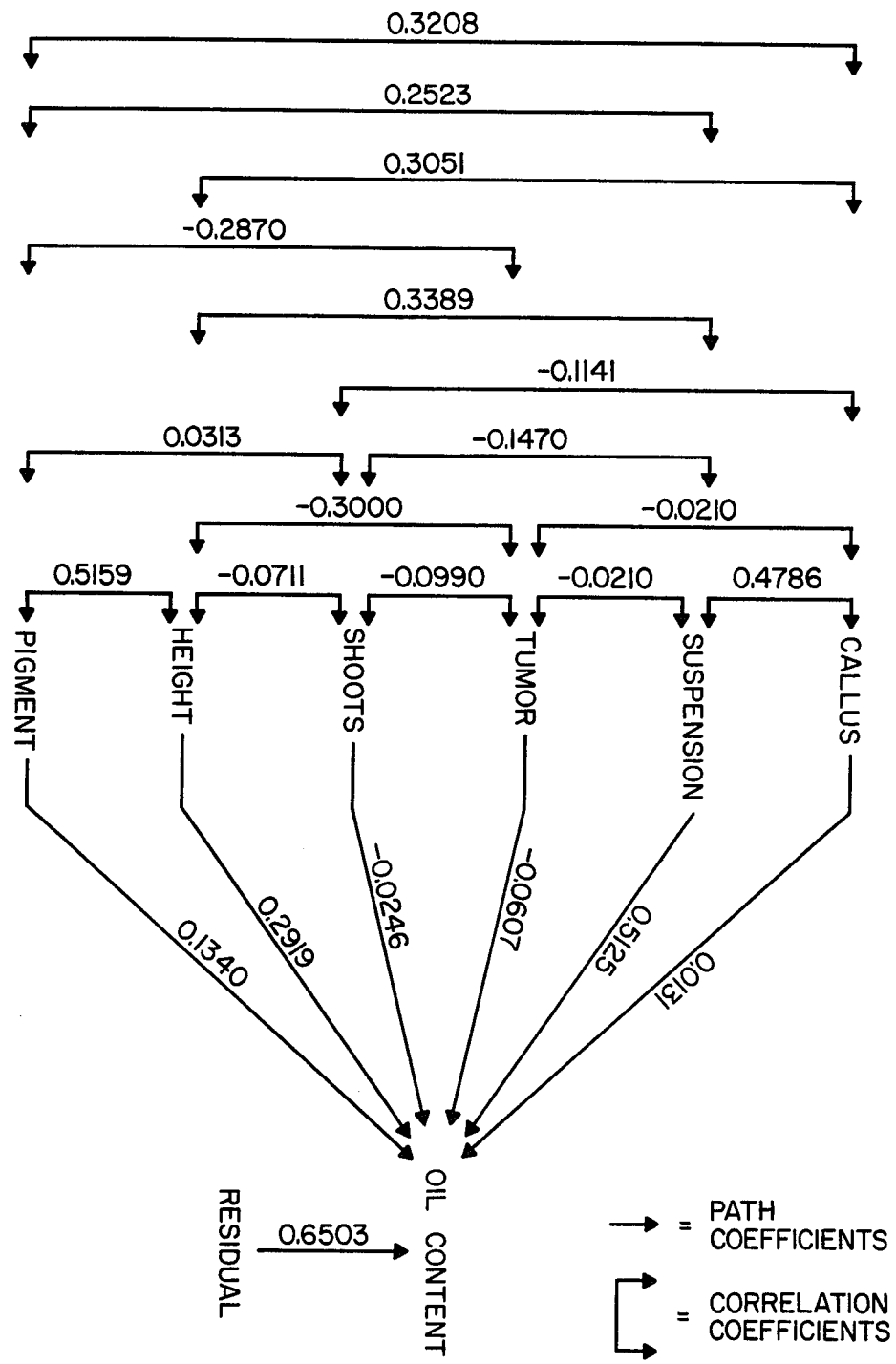
FIG. 1 is a path diagram describing associations between sunflower variables.

Only the minimal salts of the medium are based on Murashige and Skoog mineral salts medium (MS medium). MS medium is typically used for plant cell culture and is described in Murashige, T. and Skoog, F. (1962) *Physiologia, Plantarium*, 15:473-97.

The following salts are typically found in the medium:
magnesium sulfate.seven hydrate ($MgSO_4.7H_2O$)
calcium chloride.dihydrate ($CaCl_2.2H_2O$)
potassium nitrate ($KNO_3$)
ammonium nitrate ($NH_4NO_3$)
potassium phosphate ($KH_2PO_4$)
manganese sulfate.four hydrate ($MnSO_4.4H_2O$)
zinc sulfate.seven hydrate ($ZncSO_4.7H_2O$)
cupric sulfate.five hydrate ($CuSO_4.5H_2O$)
colbalt chloride.six hydrate ($COCl_2.6H_2O$)
potassium iodide (KI)
boric acid ($H_2BO_3$)
sodium molybdinum oxide.dihydrate ($NaMoO_4.2H_2O$)
ferrous sulfate.seven hydrate ($FeSO_4.7H_2O$)
sodium ethylenediaminotetracetic acid (NaEDTA)

In general, as used in the invention, the exact concentration of the salts can be varied within limits without departing from the invention. To standardize the making of the medium, however, the concentrations of the above listed minimal salts are as follows:

| | |
|---|---|
| $MgSO_4.7H_2O$ | 370 milligrams/liter (mg/l) |
| $CaCl_2.2H_2O$ | 440 mg/l |
| $KNO_3$ | 1900 mg/l |
| $NH_4NO_3$ | 1650 mg/l |
| $KH_2PO_4$ | 170 mg/l |
| $MnSO_4.4H_2O$ | 22.3 mg/l |
| $ZnSO_4.7H_2O$ | 8.6 mg/l |
| $CuSO_4.5H_2O$ | 0.025 mg/l |
| $CoCl_2.6H_2O$ | 0.025 mg/l |
| KI | 0.83 mg/l |
| $H_3BO_3$ | 6.2 mg/l |
| $Na_2MoO_4.2H_2O$ | 0.25 mg/l |
| $FeSO_4.7H_2O$ | 28.75 mg/l |
| $Na_2EDTA$ | 37.25 mg/l |

A number of vitamins are added to the medium in the following amounts:

| | |
|---|---|
| inositol | up to and including about 500 mg/l; |
| thiamine.HCl | up to and including about 40 mg/l; |
| nicotinic acid | up to and including about 0.20 mg/l; |
| pyridoxine.HCl | up to and including about 4 mg/l. |

The vitamins will generally be in an amount sufficient to sustain vigorous sustain vigorous growth of the sunflower cell suspension to be grown in the medium. Within these ranges, 100 mg/l of inositol, 40 mg/l of thiamine.HCl, 20 mg/l of nicotinic acid and 4 mg/l of pyridoxime.HCl are preferred.

Also the medium will contain plant hormones. The plant hormones which may be used include auxins and cytokinins.

Various auxin-type hormones have been used in the medium and are exemplified by naphthalene acetic acid (NAA), indole butyric acid (IBA), indoleacetic acid (IAA) and 2,4-dichlorophenoxyacetic acid (2,4-D). The auxins have been used at various concentrations in the medium and in general the results obtained vary within the range of concentrations for the auxins which have been tried. The concentration ranges for the various auxins are as follows:

| | |
|---|---|
| NAA | about 0.01–10 mg/l; |
| IBA | about 1–10 mg/l; |
| IAA | about 1–4 mg/l; |
| 2,4-D | about 0.01–1 mg/l. |

Various cytokinin type hormones have been used in the medium and are exemplified by benzyl adenine (BA), zeatin (Z), kinetin (K) and $N^6\Delta_2$ isopentyl adenine (2iP). The cytokinin hormones have also been used at various concentrations in the medium and in general the results obtained vary within the range of concentrations for the cytokinin which have been tried. The concentration ranges for the various cytokinins are generally between about 0.1 mg/l to about 10 mg/l. Generally BA and K are preferred.

In addition to the above-mentioned components the medium contains sucrose. The concentration of sucrose may vary but generally an amount sufficient to permit sustained growth of the cells will be included. Typically, the sucrose concentration will be about 3% (w/v) or about 30 grams per liter.

The cell suspension medium may also include an amount of coconut water (GibCo), in a range up to about 20% v/v of the medium. Coconut water is generally included at an optimum concentration of about 10% v/v.

Formulations for the various medium and the uses thereof will be better understood from the following examples which are intended by the inventor to be exemplary only and not limiting.

In the following examples, sunflower seeds of 100 experimental genotypes were used. The experimental sunflower genytopyes originated from diverse genetic backgrounds and had undergone at least 5 generations of inbreeding and repeated selection.

Several individual phenotypic results were selected for observation and were classified as appears in the following Table I.

Criteria for plant and seedling pigmentation appear below in the Table. Seed oil content is explained further in Example II hereinbelow. Callus induction is determined by visual comparison of the experimental lines with controls from sunflower seed lines SS 405B and 89B. Suspension culture growth is explained further in Example II hereinbelow. Tumor induction is rated by germinating seeds of each inbred for 7 days and injecting the seedlings with overnight cultures of *Agrobacterium tumefaciens* (*A. tumefaciens*) strain 15955, A208 and C58. The inoculated seedlings were grown for 7 days under Agrolites ® and hypocotyl-bearing tumors were excised and grown on agar medium. Tumor size was scored after 7 days incubation in the light. Sunflower strains displaying good tumor growth had fast-growing tumors induced by all three *A. tumefaciens* cultures. Strains displaying poor tumor growth had tumors induced by one or no *A. tumefaciens* cultures. Strains displaying intermediate growth had slow growing tumors induced by all 3 *A. tumefaciens* cultures or fast growing tumors induced by 2 of 3 *A. tumefaciens* cultures.

Adventitious shoot formation was determined by culturing four shoot apices of seedlings grown from each of the 100 sunflower strains on a shoot multiplication medium for three weeks under Agrolites ®. Formation of 5 or more adventitious shoots was scored as good shoot formation. One to five adventitious shoots were rated as intermediate shoot formation. Formation of no adventitious shoots was rated as poor shoot formation.

TABLE I

Relative Proportion of Experimental Inbreds Showing Good (A), Intermediate (B) and Poor (C) Characteristics in the Field or Tissue Culture

| | Number of Individuals in Class | | |
|---|---|---|---|
| Trait | A | B | C |
| Plant height* | 28 | 54 | 15 |
| Seed Oil Content** | 48 | 28 | 21 |
| Seedling pigmentation*** | 65 | 17 | 15 |
| Callus induction | 26 | 45 | 26 |
| Suspension culture growth | 30 | 30 | 37 |
| Tumor induction | 10 | 23 | 64 |
| Shoot regeneration | 7 | 44 | 46 |

*A = dwarf or semi-dwarf, B = medium, C = tall
**A = high > 40%, B = intermediate 35–40%, C = less than 35%
***A = purple hypocotyl, B = pink hypocotyl, C = green hypocotyl

EXAMPLE I

Seeds of the experimental 100 sunflower lines were germinated as follows:

The pericarp or hull is removed from the sunflower fruits. The seeds are removed from the fruits and sterilized for 15 minutes in 30% bleach with 1–2 drops dishwashing soap. Following rinsing in sterile distilled water, the seeds are planted in test tubes, 2 per tube, in a medium of 0.5% sucrose, 1% agar and the following salts in the concentrations indicated:

| | |
|---|---|
| $MgSO_4.7H_2O$ | 370 mg/l |
| $CaCl_2.2H_2O$ | 440 mg/l |
| $KNO_3$ | 1900 mg/l |
| $NH_4NO_3$ | 1650 mg/l |
| $KH_2PO_4$ | 170 mg/l |

The seeds are germinated in the dark for 4–5 days, followed by 1–2 days in the light. Two millimeter (mm) hypocotyl segments from the germinated seedlings are then placed on the following medium:

| | |
|---|---|
| $MgSO_4.7H_2O$ | 370 mg/l |
| $CaCl_2.2H_2O$ | 440 mg/l |
| $KNO_3$ | 1900 mg/l |
| $NH_4NO_3$ | 1650 mg/l |
| $KH_2PO_4$ | 170 mg/l |
| $MnSO_4.4H_2O$ | 22.3 mg/l |
| $ZnSO_4.7H_2O$ | 8.6 mg/l |
| $CuSO_4.5H_2O$ | 0.025 mg/l |
| $Na_2MoO_4.2H_2O$ | 0.25 mg/l |
| $CoCl_2.6H_2O$ | 0.025 mg/l |
| $FeSO_4.7H_2O$ | 28.75 mg/l |
| $Na_2EDTA$ | 37.25 mg/l |
| inositol | 100 mg/l |
| thiamine.HCl | 40 mg/l |
| nicotinic acid | 20 mg/l |
| pyridoxine.HCl | 1 mg/l |
| α-naphthaleneacetic acid | 1 mg/l |
| benzyladenine | 1 mg/l |
| sucrose | 30 grams/l |
| $H_2O$ distilled | to 1000 ml |
| pH | 6.3 |

| | |
|---|---|
| agar | 6.0 gms |

The 2 mm hypocotyl segments are cultured in the dark for 2 weeks. Friable callus is removed and subcultured on the same medium. Friable callus can be maintained on the same medium for use as suspension cell cultures.

Suspension cell cultures were initiated from each callus as follows: 1.5–2.0 grams fresh weight of callus were placed in a sterile 50 ml flask containing 15 ml of a medium having the following composition:

| | |
|---|---|
| MgSO$_4$.7H$_2$O | 370 mg/l |
| CaCl$_2$.2H$_2$O | 440 mg/l |
| KNO$_3$ | 1900 mg/l |
| NH$_4$NO$_3$ | 1650 mg/l |
| KH$_2$PO$_4$ | 170 mg/l |
| MnSO$_4$.4H$_2$O | 22.3 mg/l |
| ZnSO$_4$.7H$_2$O | 8.6 mg/l |
| CuSO$_4$.5H$_2$O | 0.025 mg/l |
| CoCl$_2$.6H$_2$O | 0.025 mg/l |
| KI | 0.83 mg/l |
| H$_3$BO$_3$ | 6.2 mg/l |
| NaMoO$_4$.2H$_2$O | 0.25 mg/l |
| FeSO$_4$.7H$_2$O | 28.75 mg/l |
| Na$_2$EDTA | 37.27 mg/l |
| inositol | 100 mg/l |
| thiamine.HCl | 40 mg/l |
| nicotinic acid | 20 mg/l |
| pyridoxine.HCl | 1 mg/l |
| α-naphthaleneacetic acid | 1 mg/l |
| benzyladenine | 1 mg/l |
| coconut water | 100 mg/l |
| sucrose | 30 grams/l |
| H$_2$O distilled | add to 1000 ml final volume |
| pH | 6.3 |
| agar | 6.0 gms |

The cultures were incubated for 14 days on a rotary shaker in low light, about 500–1000 Lux, at about 24°–28° C. Suspension culture growth was measured by packed cell volume (PCV) as follows:

Approximately 15 ml of the cell suspension was placed in a graduated centrifuge tube and spun at approximately 500 times gravity for 5 minutes. PCV was determined directly from the centrifuge tube.

EXAMPLE II

Oil content of sunflower seeds obtained from field-grown plants of the inbred sunflower seed lines tested in Example I were analyzed for correlation with growth characteristics of cells in culture.

Field tests of the seeds were conducted in Fresno, Calif. The field-grown plants were planted in May 1981 and harvested in August 1981. Plant rows were 30 inches apart and plants were spaced 9 inches apart in each row. Following harvest seeds were air-dried in a force-air dryer at 120° F. to a moisture content of <6% before measuring oil content by nuclear magnetic resonance (NMR) spectroscopy.

Sunflower seed oil was analyzed by use of a Newport Analyzer Mark IIIA NMR using procedures established by the manufacturer. A 6.5 ml sample assembly was used for sunflower samples. Samples were analyzed at room temperature using an RF level of 225 uA and an integration time of 32 seconds. Gate width used was 1 gauss. The NMR analyzer was standardized by use of a FGIS sealed sunflower seed standard. Variable weight samples were used (weights were recorded to the nearest 0.01 gram). Oil content of the sunflower seed samples was calculated with the following formulas:

$$\text{Constant} = \frac{\text{NMR reading of calibration standard}}{(\text{weight of seed}) \times (\text{oil content of standard})}$$

$$\% \text{ Oil} = \frac{\text{NMR reading of seed sample}}{(\text{weight of samples}) \times (\text{constant})}$$

The constant used for all seed samples was 0.2562.

For purposes of the correlation analysis, seed oil content data were grouped into three categories: high oil content—above 40% weight of oil/weight whole seed (w/w); intermediate oil content—35–40% w/w; and low oil content—below 35% w/w. Suspension cell growth was likewise classified into three categoreis: high growth > 10 ml PCV, intermediate growth > 6–10 ml PCV, and low growth ≦ 6 ml PCV. Seed oil content was analyzed for its correlation with suspension cell growth characteristics and callus induction by means of chi square analyses after construction of 3×3 contingency tables. A significant correlation (0.1% probability (P) level) between high suspension cell growth and high oil content was found. Based on these correlation results a screen for oil content was developed using the following criteria: Good cell growth was defined as a five-fold increase in cell growth over a 2 week growth period in the suspension culture conditions described In Example I herein. In general, 1.5–2.0 g initial callus inoculum yielded an initial PCV of 1.5–2.0 ml. Cell suspension cultures having PCVs of 7.5 ml after 14 days of suspension cell culture from initial 1.5–2.0 g callus inocula were classified as showing good growth.

A significant correlation (0.1% P level) between good callus induction and good suspension cell growth was also found. A lower, but significant, correlation between good callus induction and oil content was also found. If the total population of test seed lines is considered, 48% produced seed with oil content of 40% or greater. If the population of those seeds which gave good callus induction, as measured by callus fresh weight greater than 2 grams, is considered, 63% of strains showing good callus induction had oil contents of 40% w/w or greater. If the population of those sunflower seed lines that gave good cell suspension growth as measured by packed cell volume of about 5 times the volume of the initial callus inoculum are considered, 81% of lines showing good cell suspension growth had oil contents of 40% w/w or greater.

To determine whether the correlations between good cell growth—high oil content and good callus induction—high oil content are each directly linked correlations rather than an indirect association via a third character such as plant height, a statistical method, known as path coefficient analysis, described in *Path Analysis,* C.C.Li., Boxwood Press, Pacific Grove Ca., was applied to data collected for suspension growth, callus induction, plant height, oil content, shoot formation, tumor induction and seedling pigmentation. By means of this statistical method it is possible to partition the correlation of the above-tested characteristics into direct and indirect linkage to seed oil content.

Correlation coefficients were calculated using the Proc Corr program from the Statistical Analysis System (SAS) and multiple linear regression was performed using the Proc GLM program of SAS. Both of these programs were accessed via a Digital MINC 23 computer. The major steps in path analysis are:

(a) Normalize data by expressing each datum point as the deviation from the mean $$\left(\text{i.e. } X - \frac{\Sigma X}{n}\right).$$

(b) Use the normalized data to calculate correlation coefficients (r) between all combiantions of variables.

(c) Obtain concrete (unstandardized) regression coefficients (b) from multiple linear regression analysis.

(d) Calculate path coefficients (p) between pairs of variables from the concrete regression coefficient and the standard deviations (o) of the variables using $$p_{o1} = b_{o1} \frac{\sigma_1}{\sigma_o}.$$

(e) Calculate indirect effects via third characters, e.g., $P(\text{oil}\leftarrow\text{callus via suspension}) = P(\text{oil}\leftarrow\text{suspension}) \times (r\text{callus/suspension})$ (f) Check that the sum of direct and indirect effects is equal to the correlation coefficient, e.g.:

$$p_{o1} + p_{o2}r_{12} + p_{o3}r_{13} + p_{o4}r_{14} = r_{01} = \text{correlation between variables 0,1}$$

The path coefficients indicating the direct effect of individual characters on oil content were calculated as described above and were used to construct a simple path diagram appearing as FIG. 1, in which correlations with oil content have been replaced by path coefficients. The values of these path coefficients show that the characteristics that have a statistically significant direct effect on oil content are suspension culture growth and plant height. Thus, the significant correlations between callus induction, seedling pigmentation and oil content must have been due to indirect effects. Thus, the growth of sunflower cells in suspension culture can be used to predict the oil content of sunflower plants and is a useful tool for the production of high oil sunflower inbreds.

EXAMPLE III

Three sunflower seed lines known to have sunflower oil contents that are repeatedly high, intermediate or low were tested for correlation of suspension cell culture growth and oil content.

Seeds were germinated as in Example I above. Hypocotyl segments were sterily obtained from the germinated seedlings. Approximately 1.5 to 2.0 grams of hypocotyl segments from each seed line were used as the inoculum to initiate the suspension cell cultures instead of callus. In all other respects the cultures were carried out as in Example I. In each case, expected cell growth after fourteen days for each of the seed lines correlated with the known oil content of the seed line.

What is claimed is:

1. The method of screening sunflower seed lines for high oil content comprising:
   (a) providing sunflower tissue from seed lines whose oil content is to be screened;
   (b) providing a plant growth medium comprising:
      (1) minimal salts;
      (2) vitamins comprising;
         inositol
         thiamine HCL
         nicotinic acid
         pyridoxine HCl
      (3) plant hormones;
      (4) sucrose; and
      (5) coconut water,
   said medium being a sunflower cell suspension culture medium;
   (c) culturing said tissue in said cell suspension culture medium for a period sufficient to obtain good cell growth; and
   (d) selecting as high oil content producers those sunflower seed lines that show good cell growth wherein good cell growth is defined as about a five-fold increase in the packed cell volume of said sunflower tissue after a two week growth period.

2. The method of screening sunflower seed lines for high oil content defined in claim 1 wherein said sunflower tissue is callus.

3. The method of screening sunflower seed lines for high oil content defined in claim 1 wherein said sunflower tissue is a hypocotyl segment of a sunflower seedling.

4. The method of screening sunflower seed lines for high oil content defined in claim 1 wherein step (c) further comprises:
   i. culturing said tissue in said suspension culture medium for about 14 days on a rotary shaker in low light conditions between about 500-1000 lux;
   ii. separating remains of said tissue from said suspension culture cells; and
   iii. determining packed cell volume of said suspension culture cells.

5. The method of screening sunflower seed lines for high oil content defined in claim 4 wherein said tissue is callus.

6. The method of screening sunflower seed lines for high oil content defined in claim 4 wherein said tissue is a hypocotyl segment of a sunflower seedling.

* * * * *